United States Patent [19]

Wehling et al.

[11] Patent Number: 5,503,846

[45] Date of Patent: Apr. 2, 1996

[54] BASE COATED ACID PARTICLES AND EFFERVESCENT FORMULATION INCORPORATING SAME

[75] Inventors: Fred Wehling, New Hope; Steve Schuehle, Maple Grove, both of Minn.

[73] Assignee: Cima Labs, Inc., Minneapolis, Minn.

[21] Appl. No.: 32,677

[22] Filed: Mar. 17, 1993

[51] Int. Cl.$^6$ .............................. A61K 9/14; A61K 9/16; A61K 9/46
[52] U.S. Cl. .................... 424/466; 424/465; 424/489; 514/951; 514/970; 514/974
[58] Field of Search ..................... 424/465, 466; 514/970, 974

[56] References Cited

U.S. PATENT DOCUMENTS

| | | | |
|---|---|---|---|
| Re. 33,086 | 10/1989 | Bru | 424/44 |
| 1,764,996 | 4/1928 | Andrews | 424/44 |
| 2,147,743 | 8/1938 | Levin | 167/57 |
| 2,211,485 | 9/1938 | Zimmerman | 167/57 |
| 3,773,922 | 11/1973 | Gergely | 424/44 |
| 3,887,700 | 6/1975 | Boncey et al. | 424/44 |
| 3,993,759 | 11/1976 | Pohlke et al. | 424/250 |
| 4,083,951 | 4/1978 | Goudie et al. | 424/44 |
| 4,101,650 | 7/1978 | Umezawa | 424/44 |
| 4,127,645 | 11/1978 | Witzel et al. | 424/44 |
| 4,289,751 | 9/1981 | Windheuser | 424/35 |
| 4,678,661 | 7/1987 | Gergely et al. | 424/44 |
| 4,704,269 | 11/1987 | Korab | 424/44 |
| 4,762,702 | 8/1988 | Gergely et al. | 424/44 |
| 4,777,033 | 10/1988 | Ikura et al. | 424/44 |
| 4,824,664 | 4/1989 | Tarral et al. | 424/446 |
| 4,847,093 | 7/1989 | Ayer et al. | 424/44 |
| 4,867,942 | 9/1989 | Gergely et al. | 424/466 |
| 4,888,177 | 12/1989 | Gergely et al. | 424/466 |
| 4,897,257 | 1/1990 | Nishikawa et al. | 424/44 |
| 5,051,262 | 9/1991 | Panoz et al. | 424/468 |
| 5,087,442 | 2/1992 | Takaichi et al. | 424/44 |
| 5,102,665 | 4/1992 | Schaeffer | 424/466 |

FOREIGN PATENT DOCUMENTS

| | | |
|---|---|---|
| 0361680 | 4/1990 | European Pat. Off. . |
| 1138730 | 6/1966 | United Kingdom . |
| 2091625 | 8/1982 | United Kingdom . |
| 2093052 | 8/1982 | United Kingdom . |
| 2093376 | 9/1982 | United Kingdom . |
| 2148117 | 4/1985 | United Kingdom . |
| 2148117 | 5/1985 | United Kingdom . |
| 1274797 | 5/1992 | United Kingdom . |

*Primary Examiner*—Thurman K. Page
*Assistant Examiner*—James M. Spear
*Attorney, Agent, or Firm*—Lerner, David, Littenberg, Krumholz & Mentlik

[57] ABSTRACT

The disclosed invention includes a base coated acid formulation which is highly compressible. The disclosed invention also relates to formulations including both an effervescent couple and an acid sensitive active agent. Formulations having an acid neutralization capacity of under 5.0 are also described as are methods of making particulate base coated acid and dosage forms using same.

37 Claims, No Drawings

BASE COATED ACID PARTICLES AND EFFERVESCENT FORMULATION INCORPORATING SAME

FIELD OF THE INVENTION

The present invention relates to the field of effervescent dosage formulations and particularly those used in combination with acid sensitive active ingredients.

BACKGROUND OF THE INVENTION

Gastrointestinally active agents including antiulcerative $H_2$-antagonists are widely regarded as being useful in the treatment of ulcers and other related gastrointestinal maladies. $H_2$-antagonists such as famotidine are generally known to inhibit both gastric acid and pepsin secretion. See M. Miwa et al., *J. Clin. Pharmacol. Ther. Toxicol.*, 22, 214 (1984). See also U.S. Pat. No. 4,283,408.

It is important in administering such $H_2$-antagonists that they be released from their dosage form quickly so that their biological uptake can be hastened and peak serum levels can be achieved relatively quickly. These desires must, however, be balanced against the need for providing an acceptable dosage form in terms of taste, convenience of use, and packaging, shipping, and handling. There are a number of dosage forms that hold a good deal of promise in administering $H_2$-antagonists. However, it has been difficult to date to find a vehicle which can satisfy all of many and sometimes conflicting needs and desires for such a dosage form.

One possible vehicle for administration of these gastrointestinally active agents is the effervescent tablet. Effervescence has long been known to provide some measure of taste-masking. In addition, effervescence can provide rapid disintegration of the dosage form so as to allow for generally higher bioavailability of the active agent. In this particular instance, however, what would otherwise appear upon first blush to be an ideal dosage form for $H_2$-antagonists is, in reality, generally unsatisfactory.

Many $H_2$-antagonists, while both soluble and active in acidic solutions such as those found in the stomach, are sensitive to acid exposure during storage. As effervescence generally requires the presence of an acidic and basic component, the production of a formulation including both the acidic half of an effervescent couple and an $H_2$-antagonist is considered undesirable due to the instability of the active ingredient in the presences of an acid. For example, Schaeffer, U.S. Pat. No. 5,102,665, acknowledges the instability of the $H_2$-antagonists in the presence of, for example, citric acid, which is typically used as one of the effervescent couple. Schaeffer therefore suggests that the replacement of citric acid with monoalkali metal citrate, i.e. monosodium citrate to overcome this problem. However, in some countries, such as the United States, mono- and di-sodium salts of citric acid are not generally regarded as safe.

Base coated acids are known in the art. For example, Boncey et al., U.S. Pat. No. 3,887,700 discloses aspirin compositions which are readily and completely soluble in water. The compositions consist of an aspirin core coated with a water soluble material. The coated aspirin particles may then be combined with an effervescing couple which will facilitate dissolution of the composition in water. The coating of the aspirin particles prevents the aspirin and the alkali component of the effervescent couple from reacting prematurely, thereby increasing the stability of the compositions.

Gergely et al., U.S. Pat. No. 4,678,661, discloses an effervescent composition consisting of an organic acid crystal coated with a surface layer which includes calcium carbonate. The amount of calcium carbonate disclosed is said to be approximately stoicheometric. The coating adheres to the surface of the acid crystals by means of a bonding layer which is formed by a surface reaction between the calcium carbonate coating material and the acid crystals. Effervescent tablets including these base coated acid crystals have improved stability against moisture and are useful in preparations including aspirin, ascorbic acid, gluconic acid-delta-lactone, and multivitamin mixtures. The system described in Gergely et al. can also be used to deliver incompatible substances by forming a two-layer tablet, one portion of which includes one active substance coated on the effervescent granules and the other portion of which includes the other active substance either with or without effervescent components. See also Gergely et al., U.S. Pat. No. 4,762,702. These patents do not describe the use of base coated acid effervescent particulate in combination with $H_2$-antagonists or other highly acid sensitive gastrointestinally active components or directly mixing said components in a single layer dosage form.

There are also other problems in addition to the problem of insuring that the acid component of the effervescent couple does not degrade or otherwise interfere with the active ingredient. First, if a traditional amount of base is used, the acid neutralization capacity of the resulting dosage form is generally above 5.0. Unfortunately, such compounds are, according to the United States Food and Drug Administration, considered antacids.

Thus the resulting $H_2$-antagonists containing effervescent formulations can be classified as both antacids and $H_2$-antagonists. As such, clearance for such a formulation would need to be acquired from the United States Food and Drug Administration by the filing of what is known as a "dual claim". A manufacturer would therefore have to prove safety and efficacy of the formulation for both the active agent and the effervescent system/antacid. This is both difficult and expensive.

It may be possible to incorporate a very small amount of an effervescent couple into a formulation so as to result in an ANC of less than 5.0. However, the resulting formulation is by no means suitable as a dosage form, let alone classifiable as an effervescent formulation in any meaningful way. Certainly, the resulting formulation would have no taste-masking ability, a very slow effervescing or disintegration time, and a generally salty taste. If, however, as the present inventors have done, an effervescent formulation including an acid sensitive gastrointestinally active agent can be formulated having an acid neutralization constant which is below 5.0, then the dual claim status can be avoided and the attendant cost and difficulty can be avoided without sacrificing performance.

In addition to problems meeting various governmental regulations, it is well known that when an $H_2$-antagonist, such as cimetidine, is co-administered with antacids, there is frequently a substantial reduction in the bioavailability of the $H_2$-antagonist. See European Pat. Application No. 0,294,193. The same antacid based decrease in bioavailability is also known to occur with the administration of famotidine and Ranitidine. See Remington's Pharmaceutical Sciences, 18th Edition, Pg. 781 published by Mack Publishing Co. One non-effervescent solution proposed in that application is at least the partial granulation of the antacid with a freely water soluble solid diluent and a rapidly swellable water-insoluble disintegrant. The ability to reduce the antacid nature of the resulting formulation would therefore also be advantageous in mitigating a reduction in the co-administration based bioavailability.

British Pat. No. 1,138,730 proposes a partial reaction of crystallized citric acid and sodium bicarbonate so as to form a mixture of mono-, di- and tri-sodium salts of 1,2,3-isopropanol tricarboxylic acid with a total free acidity of from 70% to 20%. This British patent does not disclose the product of this reaction as being a base coated acid, nor does it describe its combination with acid sensitive pharmaceutical such that the resulting stability thereof can be considered.

Alternatively, Tarral et al., U.S. Pat. No. 4,824,664, disclose the preparation of effervescent compositions including $H_2$-antagonist compounds. Purportedly, Tarral et al. overcome the instability of the $H_2$-antagonist materials in the presence of the acid component of the effervescent system by providing the citric acid used in the form of a sodium or potassium dihydrogen citrate/disodium or dipotassium hydrogen citrate couple in a weight ratio of between 8:1 and about 1:10. There is, however, no disclosure of the formation of a base coated acid. Notwithstanding, more than a stoicheometric amount of base is used in comparison to the acids used in the effervescent couple. Therefore, the resulting formulation will have an acid neutralization value higher than the desirable limit of 5.0. In another approach, European Patent No. 0,361,680 suggests incorporating of morphine into the basic component of an effervescent couple. To accomplish this, the morphine sulphate is dry mixed with sodium bicarbonate and a PVP solid binder. There is, however, no disclosure of the formation of a base coated acid.

In addition to the stability of the active ingredient, the intricacies of United States governmental regulation, and the need to minimize any reduction in the bioavailability of the active ingredient, there also remains a problem of providing an effective effervescent dosage form which is convenient to take and which can withstand the rigors of tableting, packaging, and normal shipping and handling. When acid and base components of an effervescent are used in conventional ratios, it is extremely difficult to produce a tablet without the use of substantial quantities of binder and/or the application of a significant amount of pressure.

The use of binder brings with it the introduction of unnecessary ingredients to a patient, additional cost to the manufacturer and consumer, and, inevitably, additional size to the resulting formulation. This in turn impacts the size and cost of packaging and the costs of shipping.

Alternatively, the materials can be placed under extreme pressure, (i.e. 10 tons or more), in an attempt to form a coherent tablet dosage form. However, under such circumstances it is difficult to form a tablet which will not break apart in a manner commonly referred to as "end capping" delaminate or disintegrate during subsequent tableting, packaging, shipping and handling. Even when base coated acids produced in accordance with known technique are used, these problems may still persist.

SUMMARY OF THE INVENTION

In accordance with certain preferred embodiments of the present invention, there is provided a stabilized effervescent dosage form including:

a pharmaceutically active agent, and intimately mixed therewith, a particulate effervescent couple. The effervescent couple includes a solid core of an edible acid and a coating of an edible base. The amount of base used in forming the effervescent couple is less than a stoicheometric amount based on the amount of acid used. The amount of base in the resulting base coated acid is also thought to be less than a stoicheometric amount. The edible acid core and the edible base coating are formed such that at least some free unreacted edible acid remains. In a particularly preferred embodiment, the pharmaceutically active agent is acid sensitive. The coating of base on the acid retards reaction between the edible acid and the acid sensitive pharmaceutically active agent. This dosage form preferably has an Acid Neutralization Capacity of under 5.0.

In a particularly preferred embodiment, the pharmaceutical agent is a gastrointestinally active agent such as an $H_2$-antagonist. The use of the base coated acid of the present invention therewith will not compromise the stability of the active ingredient.

The resulting dosage forms are stable, effervescent, and rapidly dissolvable. They also do not compromise the bioavailability of certain pharmaceutical agents and are not subject to "dual claim" status. Tablets produced using these formulations are readily compressible and require only a minimum level of tableting aids. Rapid disintegration, good taste-masking, and easy administration result from these formulations.

In accordance with other preferred aspects of the present invention, there is provided a process of producing a highly compressible particulate effervescent couple. The process includes charging at least one particulate edible acid and at least one particulate edible base into a reactor. The edible base generally has a particle size which is less than the particle size of the particulate edible acid. The particulates are then mixed while adding liquid to the particulate in the reactor while the mixing continues. The particulates are then allowed to react in the presence of the liquid for a period of time so as to form a coating of the edible base substantially completely around the particulate edible acid. Vacuum and heat are next applied to the reactor while physically tilting the reactor. The heat and vacuum provide for rapid and even deliquification of the particulate. The tilting of the reactor prevents a coating of the edible base from being abraded from the particulate edible acid. Finally, the particulate is discharged. By this process the particulate edible acid has been substantially completely coated with the edible base.

The stable, highly compressible particulate effervescent couple resulting from the use of this process is also a highly preferred aspect of the present invention.

In accordance with yet another preferred embodiment of the present invention, there is provided a process of making an effervescent tablet. The process includes several steps. The first step involves mixing an active agent with a particulate effervescent couple produced as previously described, wherein the ratio of the active agent to the particulate effervescent couple ranges from between about 1:300 to about 1:0.25; and compressing the mixture in a tablet press under a pressure of between about 0.2 to about 10 tons. The resulting effervescent tablet is relatively rapidly dissolvable in the mouth or in liquid while at the same time being capable of withstanding conventional packaging, shipping, and handling without cracking, end capping, or disintegrating.

Optionally, up to about 1.5 weight percent of lubricant and up to about 15 weight percent of binder may be utilized.

In other related preferred embodiments, the process can be used to produce tablets which incorporate acid sensitive gastrointestinally active agents such as $H_2$ antagonists and have an ANC of under 5.0.

Tablets produced in accordance with this process are also a highly preferred embodiment of the present invention.

In accordance with another preferred embodiment of the present invention, there is provided a tableting lubricant specifically adapted to be used in the tableting of effervescent tablets designed to be dissolved in a liquid prior to ingestion. The lubricant includes at least one stearate, at least one surface active agent and at least one polyol, each present in an amount which is effective to ensure that the tablets do not bind during formulation in a tablet press, and to ensure that the resulting effervescent liquid is not cloudy and does not either scum or foam. It has been found that this lubricant is effective, without scumming, clouding or foaming in liquid dosage forms resulting from liquid dissolvable tablets.

Some of the preferred embodiments of the present invention overcome the myriad of problems of the prior art by providing a unique effervescent dosage form including an acid sensitive gastrointestinally active agent utilizing a particulate effervescent couple of an edible acid substantially homogeneously coated with an edible base which nonetheless has an acid neutralization capacity of less than 5.0. In addition, a particularly efficacious particulate base coated acid has been developed which can be used in the formation of effervescent dosage forms but which does not require the use of extraordinarily high compression pressure or the use of undesirably large quantities of binder. Formulations incorporating this particular effervescent couple are therefore able to achieve not only the desire to stability and acid neutralization capacity, but also the size, shape and hardness necessary to survive normal packaging and handling while at the same time providing a tablet which is neither intimidating to the consumer or too slow in disintegration of the dosage form to be generally useful.

DETAILED DESCRIPTION OF THE PREFERRED EMBODIMENT

The term "pharmaceutical(s)" in accordance with this aspect of the present invention means a drug. Pharmaceutical(s) may include, without limitation, antacids, analgesics, anti-inflammatories, antibiotics, laxatives, anorexics, anti-asthmatics, antidiarrhetics, antiflatulents, antimigraine agents, antispasmodics, sedatives, antihyperactives, tranquilizers, antihistamines, decongestants, betablockers, and combinations thereof.

The term "pharmaceutical(s)" as used herein may also include such compounds as vitamins, minerals and dietary supplements.

As used in this disclosure, the term "vitamin" refers to trace organic substances that are required in the diet. For the purposes of the present invention, the term "vitamin(s)" include, without limitation, thiamin, riboflavin, nicotinic acid, pantothenic acid, pyrdoxine, biotin, folic acid, vitamin $B_{12}$, lipoic acid, ascorbic acid, vitamin A, vitamin D, vitamin E and vitamin K. Also included within the term "vitamin" are the coenzymes thereof. Coenzymes are specific chemical forms of vitamins. Coenzymes include thiamine pyrophosphates (TPP), flavin mononucleotide (FMM), flavin adenine dinucleotide (FAD), Nicotinamide adenine dinucleotide (AND), Nicotinamide adenine dinucleotide phosphate (NADP) Coenzyme A (CoA) pyridoxal phosphate biocytin, tetrahydrofolic acid, coenzyme $B_{12}$, lipollysine, 11-cis-retinal, and 1,25-dihydroxycholecalciferol. The term "vitamin(s)" also includes choline, carnitine, and alpha, beta, and gamma carotenes.

As used in this disclosure, the term "mineral" refers to inorganic substances, metals, and the like required in the human diet. Thus, the term "mineral" as used herein includes, without limitation, calcium, iron, zinc, selenium, copper, iodine, magnesium, phosphorus, chromium and the like, and mixtures thereof.

The term "dietary supplement" as used herein means a substance which has an appreciable nutritional effect when administered in small amounts. Dietary supplements include, without limitation, such ingredients as bee pollen, bran, wheat germ, kelp, cod liver oil, ginseng, and fish oils, amino-acids, proteins and mixtures thereof. As will be appreciated, dietary supplements may incorporate vitamins and minerals.

As will be appreciated, in accordance with one preferred aspect of the present invention, a dosage form which is particularly useful for the delivery of acid sensitive pharmaceuticals as defined herein has been discovered. An "acid sensitive pharmaceutical" is a pharmaceutically active compound which could break down, degrade or be inactivated, either in whole or in part, as a result of being formulated directly with an acidic component typically used in an effervescent couple. Many such acid sensitive pharmaceuticals are known in the art. For example, without limitation, Thrombin is described as being acid sensitive in U.S. Pat. No. 5,134,229. Hormones such as insulin, ACPH, TSH, STH, calcitonin, other compounds such as interferon, enzymes such as Factor VIII and immunological agents such as vaccines are disclosed as being acid sensitive compounds in U.S. Pat. No. 5,032,405. PR-21-aceylated dopamine bonded to a reduced dihydropyridine/pyrdium salt is disclosed as being acid sensitive in U.S. Pat. No. 4,976,968. Penicillin G is disclosed as being acid sensitive in U.S. Pat. No. 4,568,547 and other compounds such as erythromycin, penicillin, clorazepate, digitalis glycosides, cephalosporins, novobiocin and pancreatin are described in U.S. Pat. No. 4,863,741 as being acid sensitive pharmaceutical compounds.

The term "acid sensitive gastrointestinally active agent" in accordance with the present invention means an active ingredient, such as a pharmaceutically active compound which could break down, degrade, or be inactivated either in whole or in part, as a result of being formulated directly with an acidic component typically used in an effervescent couple. By "gastrointestinally active", it is understood that the acid sensitive compounds in accordance with a preferred aspect of the present invention will be active in the digestive system of a patient. These active agents may include anti-ulceratives such as $H_2$-antagonists, antidiarrhetics, antiflatulents, diagnostic agents, gastrointestinal motility factors, laxatives, and the like. $H_2$-antagonists in accordance with the present invention include, without limitation: cimetidine, famotidine, ranitidine, nizatidine, etintidien, lupitidine, mifentidien, niperotidine, roxatidine, sufotidine, tuvatidine and zaltidine in their free forms, as stable salts and mixtures thereof.

The terms "effervescent agent(s)" or "effervescent couple" in accordance with the present invention include compounds which evolve gas. The preferred effervescent agents evolve gas by means of chemical reactions which take place upon exposure to a liquid such as water and/or to saliva in the mouth. This bubble or gas generating chemical reaction is most often the result of the reaction of a soluble edible acid and an alkali metal carbonate/dicarbonate or edible base. The reaction of these two general classes of compounds produces carbon dioxide gas upon contact with a liquid, and in particular, water. These water activated materials should be kept in a generally anhydrous state with little or no absorbed moisture or in a stable hydrated form since exposure to water will prematurely disintegrate the tablet.

The "edible acid" in accordance with the present invention may be any acid which is safe for human consumption and may generally include food acids, acid anhydrides and acid salts. Food acids include citric acid, tartaric acid, malic acid, fumaric acid, adipic acid, and succinic acids, etc. Acid anhydrides of the above described acids may also be used. Acid salts may include sodium, dihydrogen phosphate, disodium dihydrogen pyrophosphate, acid citrate salts and sodium acid sulfite. When the formulations in accordance with the present invention are designed so as to have an acid neutralization capacity of less than 5.0, it is preferred that the edible acid be a crystallized citric acid.

Carbonate sources include dry solid carbonate and bicarbonate salts such as sodium bicarbonate, sodium carbonate, potassium bicarbonate and potassium carbonate, magnesium carbonate and sodium sesquicarbonate, sodium glycine carbonate, L-lysine carbonate, arginine carbonate and amorphous calcium carbonate. Potassium and sodium bicarbonate are particularly preferred, especially when the formulation is to have an acid neutralization capacity of under 5.0.

As previously described, it is highly desirable when administering gastrointestinally active agents and, in particular, $H_2$-antagonists, that the dosage form have an acid neutralization capacity or "ANC" of under 5.0. Acid neutralization capacity is defined in the food and drug regulations of the United States of America, 21 C.F.R. § 331.10, Part 330, Subpart B as the quantity of hydrochloric acid, measured in milliequivalents, that an active antacid ingredient is capable of neutralizing.

In general, the ANC is determined by the amount of free acid remaining after reaction with the base when balanced against the amount of base remaining. However, to a lesser degree, the amount of the effervescent couple used in the resulting dosage form may also play a role in determining the ANC.

The inventors have found that, as a practical limit, about 1300 mg of effervescent couple in accordance with the present invention is as much material as the dosage forms can include while maintaining an ANC of under 5.0. Above about 1300 mg, the resulting formulations have an ANC of 5.0 or over. Of course, this is measured by the standard tests recited as of the filing date hereof in Title 21. Larger quantities of effervescent couple in accordance with the present invention may also be used if an ANC of under 5.0 is not a factor of concern or if other ANC test methods are utilized. By an ANC of under 5.0, it is understood that an ANC of from between about 0.2 and just under 5.0 is contemplated. Preferably, however, the ANC ranges from about 2.0 to about 4.5.

In a preferred aspect of the present invention, the base coated acid particulate is formulated using less than a stoicheometric amount of base when compared to the amount of acid used. Therefore, the amount of edible base will not be sufficient to react with all of the carboxyl groups of the edible acid and some free, substantially unreacted acid will inevitably remain. Presumably, the resulting coating conserves the non-stoicheometric relationship of the acid and base.

The particulate effervescent couple of the present invention, also referred to herein as "base coated acid", is useful in preparing a rapidly disintegrating tablet. The latter is true because particulate effervescent couple produced in accordance with the present invention has several properties heretofore unknown in partially reacted base acids effervescent couples.

For example, the particulate is highly compressible and therefore can be used in large quantities. By the incorporation of large quantities of such a base coated acid, it is possible to generate a good deal of effervescence thereby hastening disintegration times and providing considerable taste-masking power. Generally larger quantities of other effervescent couples may be required by other formulations. Furthermore, because of the compressibility of the base coated acid of the present invention, it is unnecessary to use the quantity of binder and other adjuvants normally associated with effervescent tablets, particularly those utilizing other forms of effervescent couple. Alternatively, tablet dosage forms in accordance with the present invention can be produced without the need for a great deal of compression. This also ensures a rapid disintegration time. This is particularly surprising because free citric acid, and, to a lesser degree, free carbonates and bicarbonates are not very compressible. Usually, formulations including these free forms require high quantities of binders and/or high levels of compression. As the effervescent couple of the present invention includes at least some free, substantially unreacted acid, it would be expected that the effervescent couple and the resulting tablets would not be very compressible. But surprisingly, they are. Finally, and as previously described, the particulate effervescent couple formed in accordance with the present invention can be formulated so as to have an acid neutralization capacity of less than 5.0.

The particulate effervescent couple in accordance with the present invention may be produced by charging at least one particulate edible acid and at least one particulate edible base into a reactor. Any edible acid in any edible base may be used. However, when the acid neutralization value of the resulting particulate is to be maintained under 5.0, it is preferred that the acid used be citric acid or, possibly, malic acid. The choice of the carbonate source or edible base is not critical. However, it is preferred that sodium or potassium bicarbonate be utilized. The particulate is mixed by use of a chopper blade and propeller. Thereafter, liquid and, in particular, water, is added to the particulate while the particulate is still mixing within the reactor.

The liquid addition begins the reaction of the edible acid and edible base such that the edible base begins to coat the individual crystals of the edible acid. Specific steps should be taken to ensure that the base coating is uniformly applied to the surface of the edible acid crystals and is not abraded or rubbed off. Of course, there are any number of methods of accomplishing this, including the use of specific types of agitation. However, it has been found particularly useful to employ a reactor which can be tilted periodically during processing. It has been found that a Zanchetta model ROTO-600-P reactor is particularly useful for this purpose. The reactor is periodically tilted to an angle of greater than about 75° from vertical, or more. More preferably, the reactor will be tilted to as much as 180°, 90° from vertical in two opposed direction. It is also preferable to tilt the reactor at least once every 5 minutes and more preferably, at least once per minute.

Tilting can occur throughout the process. However, it is preferably used after the particulate and liquid have had time to react. Often, tilting occurs coincidentally with the application of additional heat and/or vacuum.

After sufficient reaction has taken place, vacuum and heat are applied to the reactor, while agitation and tilting continues to drive off the liquid and stop the continued chemical reaction between the edible acid and the edible base. The drying process should also be undertaken so as to minimize the abrasion of the coating. When sufficient water has been removed so as to stop the reaction and after the acid crystals have been homogeneously coated with base, the material can be cooled and discharged for subsequent formulation. Of course, in some embodiments, heat is applied before the vacuum.

The edible acid, as previously discussed, useful in accordance with the present invention, is preferably crystalline in form having highly discrete crystals of a particle size such that 100% thereof will be retained upon a 60 mesh screen or larger. The edible base is generally in the form of a powder having a particle size such that 99% of the particulate thereof will pass through a 100 mesh screen. The base particles are typically smaller than their particulate acid counterparts.

The ratio of particulate edible acid to powder edible base charged to the reactor will, in large degree, control the size and composition of the resulting particulate couple. The degree that the reaction between the edible acid and edible base are allowed to continue will also contribute to the structure and behavior of the resulting formulations.

In accordance with the present invention, it is preferred that the amount of edible base used be less than a stoicheometric amount when compared to the amount of edible acid used. Therefore, the amount of edible base will not be sufficient to react with all of the carboxyl groups of the edible acid and some free, unreacted acid will inevitably remain. More preferably, between about 44% and about 60% of the particulate charged to the reactor by weight is edible acid and between about 56% and about 40% of the particulate charged to the reactor is edible base. Where an ANC of under 5.0 is desired, between about 49% and about 60% of the particulate charged to the reactor by weight is edible acid and between about 51% and about 40% of the particulate is edible base. More preferably, between about 52% and about 56% of the particulate charged to the reactor is edible acid and between about 44% and about 48% of the particulate is edible base. These percentages are by weight based upon the use of citric acid and sodium or potassium bicarbonate.

Of course, acid and base equivalents can be calculated by those of ordinary skill and equivalent weights of other acids and bases derived. For example, the amount of base used should not react all of the edible acid. At a minimum, the number of acid groups should exceed the amount of available base by 30% or more.

In accordance with a particularly preferred embodiment, in accordance with the present invention, the liquid which is added to facilitate the reaction of the edible acid and edible base is water. The amount of liquid added to the particulate generally ranges from between about 1 to about 20 ml/kg (based on the weight of the starting material), but preferably ranges from between about 8 to about 12 ml/kg. Although the liquid may be added in one single step, it is preferred that the liquid be added gradually over a period of time ranging from between about 1 to about 8 minutes. Water may be added as one or more fine streams or as a mist. In addition, it may be possible to introduce liquid into the reactor in a plurality of discrete steps such as applying a certain volume in a certain period of time followed by a period of time where no further liquid is added. Thereafter, the same or a different amount of liquid can be added at the same or a different rate. Generally, however, the rate of liquid addition to the reactor is between about 0.3 and about 0.9 liters per minute.

For example, after the edible acid and edible base are charged to the mixer and the chopping blade is inserted, mixing begins. Thereafter about 6 ml per kg of water is added to the mixture over a 2 minute interval. The mixture is allowed to react while mixing continues for about 3 minutes. Then about 6 ml per kg of additional water is added over a 2 minute period. The mixture is then allowed to react for an additional 11 minutes. Thereafter, the reaction is stopped by the application of heat and vacuum. This drives out the added liquid essentially fixing the partially reacted acid and base.

Neither the speed nor sequence of liquid addition is that critical. Of course, the more gradual the addition of water, the more gradual the reaction and the more gradual the build-up of base coating or the acid crystals. This is generally believed to be advantageous. However, the greater the exposure to liquid, the greater the degree of dissolution of the acid and base particulate. This is to be controlled. The reaction time is also a factor of the size of the reactor, the ratio of particulate acid and base, and quantity of ingredients, Generally, reaction times of 1 to 20 minutes prior to the application of vacuum and/or heat are used.

The most important consideration appears to be the end point of the reaction. If the reaction does not progress sufficiently, then an inadequate degree of coating will be realized. The stability of acid sensitive agents combined with such particulate is thereby jeopardized.

If, on the other hand, the reaction continues for too long, then the resulting effervescent couple will not have at least some free, unreacted acid remaining. The presence of a core of such free acid is preferable. The reaction would not be reliably controllable and useful particulate would not be obtainable. Most importantly, however, the ANC of the resulting particulate would be over 5.0.

By free, substantially unreacted acid remaining, it should be understood that some of the many particles produced may be totally reacted, while others may have very little base coating. On the whole, however, the vast majority of particles will have a full coating and at least some identifiable acid core.

Thus, instead of prescribing a series of reaction times and conditions, it is possible to monitor the reaction for an appropriate end point. When the end point is reached, the vacuum and heat can be applied to stop the reactor. The individual end points will vary with such variable factors as size of the reactor, speed of liquid addition, quantity of added water, quantity of added ingredient, ratio of acid and base particulate degree of reaction desired, and the like. In any event, however, one way to gauge the reaction so as to determine the end point is by measuring the amount of evolved $CO_2$. Procedures for such measurements are known in the art as exemplified in Tarral et al., U.S. Pat. No. 4,824,664.

The reactor is generally heated to a temperature of between about 60° C. to about 100° C. to drive off the liquid used. Of course, the temperature used may vary depending upon the amount of vacuum applied, depending on the characteristics of the liquid used and, also, as a function of the speed at which drying is to be accomplished. More preferably, however, temperatures of between about 80° C. to about 95° C. are utilized. Similarly, the vacuum applied is such that the pressure within the reactor is below atmospheric pressure. However, more preferably, the amount of vacuum applied provides a pressure within the reactor which is between about 18 and about 29 inches of mercury.

The base coated acid effervescent couple prepared in accordance with the present invention as explained in the preceding paragraphs can be used in the formulation of a variety of effervescent dosage forms. Certainly, any of the dosage forms commonly associated with effervescence such as powders, liquid dissolvable tablets, and orally dissolvable tablets are contemplated. In addition, where practical, dosage forms may include gums, lozenges, and the like.

By virtue of the base coated acid formulated in accordance with the present invention, dosage forms can be produced which are stable, compressible and dissolvable while at the same time providing both sufficient taste-masking and an ANC of under 5.0. This renders the base coated acid formulation particularly useful in producing effervescent dosage forms that will directly incorporate acid sensitive compounds and in particular $H_2$ antagonists. Stability, as used herein, is defined as the absence of degradation of more than 5% of the active ingredient(s) over time. Degradation levels of the acid sensitive pharmaceutical active agents below about 3% are preferable. In general, degradation can be measured under accelerated condition as described later. Of course, by use of the effervescent couple of the present invention, concern for the stability of an acid sensitive compound included in the formulation is minimized. In fact, irrespective of the amount of base coated acid of the present invention used, the acid sensitive material is maintained apart from the acid component of the effervescent couple. Stability problems resulting from the interaction of the acid of the effervescent couple of the present invention and an acid sensitive ingredients intimately mixed therewith are virtually eliminated.

One formulation in accordance with the present invention is the effervescent powder mixture. Powders can be designed for direct oral administration. However, more commonly, these powders are spooned into, for example, a glass of cold water (40 mls to 100 mls) for dissolution therein. Generally, effervescent powders require the active or pharmaceutical agent to be delivered, an effervescent couple and some form of flavorings/taste-masking system. Of course, the effervescence will provide some measure of taste-masking. However, for particularly distasteful medicaments, such as $H_2$ antagonists, the use of conventional flavorings may also be advantageous. Colorants may also be added as desired.

As previously described, assuming that the intended ANC of the resulting formulation is to be maintained at less than 5.0, the effervescent couple of the present invention should be used in an amount not to exceed about 1,300 mg. Of course, this is based on an ANC measurement using the standard tests currently prescribed by Title 18.

Because of convenience, tablets often offer a more attractive dosage form. One form of tablet is the liquid dissolvable tablet designed to be dissolved in a glass of liquid. Liquid dissolvable tablets in accordance with the present invention generally comprise the effervescent couple in accordance with the present invention, the active pharmaceutical agent being delivered and a suitable flavoring such as described above with regard to effervescent powders. In addition, the base formulation should include excipients such as tableting lubricants which will allow for proper tableting. Specific tableting lubricants are described elsewhere.

Tablets designed to dissolve in liquid prior to ingestion can be of any size or shape. However, generally such tablets are between about ½" and about 1" in diameter and between about 0.12" and about 0.25" in thickness. The weight of such tablets generally ranges from between about 600 mg to about 4000 mg in total weight. The tablet can include surface markings, cuttings, grooves, letters and/or numerals for the purposes of decoration or identification.

As was true in the powdered formulations previously described, the quantity of effervescent couple utilized in the formulation for a single dose depends upon the amount of pharmaceutical agent to be delivered, the degree of effervescence desired, the desirability of maintaining an ANC of less than 5.0 and the type of effervescent couple used. However, when utilizing the base coated acid effervescent couple in accordance with the present invention, and if the ANC is to be maintained at less than 5.0, the amount of effervescent base coated acid particulate should not exceed about 1300 mg.

When using the effervescent formulations of the present invention, certain other benefits in terms of tableting inure. Specifically, because of the compressibility of the particulate effervescent couple described herein, tablets do not need to be compressed under as much pressure nor include as much binder as would otherwise be necessary. Nonetheless, the resulting tablet formulations are sturdy enough to survive tableting, shipping and handling, and, at the same time, rapidly dissolve.

Tablets can also be designed so as to be useful for direct oral administration to a patient. In a tablet for direct oral administration, the effervescent couple releases gas within the patient's mouth. This provides a pleasing organoleptic effect which very substantially masks the taste of unpalatable active ingredients in the tablet. Moreover, the effervescent action materially speeds disintegration of the tablet in the mouth, and stimulates saliva production which in turn further promotes disintegration. Many benefits attainable through the use of effervescent tablets dissolvable in the mouth are set forth in previously cited U.S. Pat. No. 5,178,878.

These tablets, like tablets designed to be dissolved in liquid prior to ingestion, can include, in addition to the effervescent couple of the present invention and the pharmaceutically active agent, colorants, flavorings and excipients such as tableting lubricants. The types of lubricants and amounts thereof are described elsewhere.

The amount of effervescent couple will depend on the same factors identified above with regard to the liquid dissolvable effervescent tablet formulation. Direct orally administered tablets according to the present invention should contain an amount of particulate effervescent couple which is effective to aid in the rapid and complete disintegration of the tablet when administered. By "rapid", it is understood that the tablets of the present invention should disintegrate in the mouth of a patient in less than 10 minutes, and desirably between about 30 seconds and about 7 minutes. In a particularly preferred embodiment according to the present invention, the tablet should dissolve in the mouth in between about 30 seconds and about 5 minutes.

Put another way, if the effervescent dosage forms in accordance with the present invention are intended for direct oral administration, i.e. the tablet placed directly in the mouth, then the amount of particulate effervescent agent present in the tablet should be effective to provide an effervescent sensation in the mouth of the patient who consumes the tablet. Thus, the patient should be able to perceive a distinct sensation of "fizzing" or bubbling as the tablet disintegrates in the mouth. To provide this sensation, the amount of effervescent agent in each tablet desirably is arranged to provide about 20 to about 60 $cm^3$ of gas. The "fizzing" sensation substantially enhances the organoleptic effects of the tablet. Thus, the amount of effervescent disintegration agent useful in accordance with the present invention is also an amount effective to provide a positive organoleptic sensation to a patient. A "positive" organoleptic sensation is one which is pleasant or enjoyable and which can be perceived readily by a normal human being.

Again, if an ANC of under 5.0 is desirable, and currently mandated testing protocols are used for ANC determination, then no more than about 1300 mg of base coated acid can be used. However, practically speaking, it is unlikely that a single orally dissolvable tablet would include 1300 mg of effervescent couple. In fact, even if the formulation were administered through the use of two separate tablets, it is unlikely that a full 1300 mg would be distributed amongst those two tablets. The direct administration of so large a quantity of effervescent material, particularly material which is as active as the effervescent particulate in accordance with the present invention, might actually produce undesirable foaming in the mouth of the patient and may be organoleptically displeasing.

The size of the orally administered tablet should be such as they are acceptable to the average consumer and may take any shape desirable. With reference to generally circular or disc shaped tablets, the diameter should be less than about $11/16$". In the context of an elongated tablet, the length should not be more than about $7/8$". The weight of the tablet should generally be less than about 2 grams and, more preferably, less than about 1.5 grams. Again, because of the improved properties of the particulate effervescent couple described herein, it is possible to formulate dosage forms, and in particular, pharmaceutical tablets which are effervescent and which rapidly dissolve in the mouth without the need for a significant quantity of binder or high compression during tableting. Therefore, the weight and size of the tablet can be kept to a minimum. Moreover, because of the relatively low pressure needed to produce effervescent tablets in accordance with this aspect of the present invention, the disintegration time of the resulting tablet can be minimized.

Within reason, there is no particular ratio of effervescent agent to active or pharmaceutical ingredient which need be adhered to for any dosage form. Generally, the amount of effervescent couple used depends upon the need for an ANC of under 5.0, the type of dosage form, and the amount and type of active agent to be administered. Broadly speaking, the ratio of active agent to effervescent couple in accordance with the present invention is from between about 1:300 to about 1:0.25. More preferably, the ratio of active agent to base coated acid is from about 1:230 to 1:1. Even more particularly, the ratio of these ingredients can be from between about 1:125 to about 1:10. Highly preferred ratios of about 1:100 to about 1:25 are also useful.

Tablets according to the present invention may include microparticles or other discrete inclusions. These typically are more slowly soluble than other tablet ingredients. As used in this disclosure, the term "complete disintegration" of the tablet does not require dissolution or disintegration of such microcapsules or other discrete inclusions.

The dosage forms of the present invention may further include one or more additional adjuvants which can be chosen from those known in the art including flavors, dilutents, colors, binders, filler, compaction vehicles, and non-effervescent disintegrants.

Examples of binders which can be used include acacia, tragacanth, gelatin, starch, cellulose materials such as methyl cellulose and sodium carboxy methyl cellulose, alginic acids and salts thereof, magnesium aluminum silicate, polyethylene glycol, guar gum, polysaccharide acids, bentonites, sugars, invert sugars and the like. As with all adjuvants, this addition adds cost, mass and additional formulation steps. Therefore, it is always desirable to keep their inclusion to a minimum.

In fact, by the use of the base coated acid particulate of the present invention, it may be possible to eliminate the use of any binder material. When binder is used, however, the amount used ranges from between about 2% and about 15% by weight of the total formulation.

Non-effervescent disintegrants include starches as corn starch, potato starch and modified starches thereof, sweeteners, clays, such as bentonite, microcrystalline cellulose, alginates, gums such as agar, guar, locust bean, karaya, pecitin and tragacanth. Disintegrants may comprise up to about 20 weight percent and preferably between about 2 and about 10 percent of the total weight of the composition.

Coloring agents may include titanium dioxide, and dyes suitable for food such as those known as F.D. & C. dyes and natural coloring agents such as grape skin extract, beet red powder, beta-carotene, annato, carmine, turmeric, paprika, etc. The amount of coloring used may range from about 0.1 to about 3.5 weight percent of the total composition.

Flavors incorporated in the composition may be chosen from synthetic flavor oils and flavoring aromatics and/or natural oils, extracts from plants, leaves, flowers, fruits and so forth and combinations thereof. These may include cinnamon oil, oil of wintergreen, peppermint oils, clove oil, bay oil, anise oil, eucalyptus, thyme oil, cedar leave oil, oil of nutmeg, oil of sage, oil of bitter almonds and cassia oil. Also useful as flavors are vanilla, citrus oil, including lemon, orange, grape, lime and grapefruit, and fruit essences, including apple, pear, peach, strawberry, raspberry, cherry, plum, pineapple, apricot and so forth. Flavors which have been found to be particularly useful include commercially available orange, grape, cherry and bubble gum flavors and mixtures thereof. The amount of flavoring may depend on a number of factors, including the organoleptic effect desired. Flavors may be present in an amount ranging from about 0.3% to about 3.0% by weight based upon the weight of the composition. Particularly preferred flavors are the grape and cherry flavors and citrus flavors such as orange.

As noted in Chapter 6 of *Pharmaceutical Dosage Forms: Tablets*, Volume 1, Second Edition, edited by Herbert A. Lieberman et al., Copyright 1989 by Marcel Dekker, Inc., lubricants normally are used in manufacture of effervescent tablets. Without the use of an effective lubricant, tableting by use of high speed equipment would be difficult. Effervescent formulations are inherently difficult to lubricate due to both the nature of the raw materials and the requirement that the tablets disintegrate rapidly.

Lubricant, as used herein, means a material which can reduce the friction arising at the interface of the tablet and the die wall during compression and ejection thereof. Lubricants may also serve to prevent sticking to the punch and, to a lesser extent, the die wall as well. The term "antiadherents" is sometimes used to refer specifically to substances which function during ejection. As used in the present disclosure, however, the term "lubricant" is used generically and includes "antiadherents". Tablet sticking during formation and/or ejection may pose serious production problems such as reduced efficiency, irregularly formed tablets, and non-uniform distribution of intended agents or ingredients to be delivered thereby. These problems are particularly severe with high speed tableting approaches and methods.

Lubricants may be intrinsic or extrinsic. A lubricant which is directly applied to the tableting tool surface in the form of a film, as by spraying onto the die cavity and/or punch surfaces, is known as an extrinsic lubricant. Although extrinsic lubricants can provide effective lubrication, their use requires complex application equipment and methods which add cost and reduce productivity.

Intrinsic lubricants are incorporated in the material to be tableted. Magnesium, calcium and zinc salts of stearic acid have long been regarded as the most efficient intrinsic lubricants in common use. Concentrations of one percent or less are usually effective.

Other traditional intrinsic lubricants include hydrogenated and partially hydrogenated vegetable oils, animal fats, polyethyleneglycol, polyoxyethylene monostearate, talc, light mineral oils, sodium benzoate, sodium lauryl sulphate, magnesium oxide and the like. See European Patent Application No. 0,275,834, the disclosure of which is incorporated by reference. See also Leal, et al., U.S. Pat. No. 3,042,531.

Lubricants, according to the present invention, may be used in an amount of up to 1.5 weight percent and preferably between about 0.1 and about 1.0 weight percent of the total composition.

Intrinsic lubricants pose certain serious difficulties when used in conventional tablets. Many lubricants materially retard the disintegration of non-effervescent tablets. In dissolution of conventional effervescent tablets, the lubricant may cause "scumming" and/or agglomeration. Stearates, for example, leave an objectionable "scum" when an effervescent tablet is placed in a glass of water. This "scum" reduces the aesthetic appeal of the solution made from an effervescent dosage form. However, when the tablets of the present invention are designed to dissolve in the mouth, the solution is never seen by the user. Therefore, the propensity of a lubricant to "scum" is unimportant. Thus, lubricants which can cause dissolution or scumming problems in other dosage forms can be used in dosage forms according to the present invention without material adverse effect. However, when the tablets of the present invention are designed for other routes of administration, such as by dissolving in a glass of water, the scumming problem remains. A particularly effective lubricant manufactured by CIMA Labs., Inc. of Minneapolis, Minn., and sold under the trademark AUTOTAB® will not scum. This lubricant, described in U.S. patent application Ser. No. 667,557, filed on Mar. 11, 1991, naming Wehling et al. as inventors, the text of which is hereby incorporated by reference, is useful in any tableting application.

Interestingly, and as described in the aforementioned Wehling et al. patent application, certain lubricant formulations are generally considered undesirable for, in particular, liquid dissolvable effervescent tablet. For example, magnesium stearate which is commonly used as a tableting lubricant, tends to yield a cloudy liquid and scum which forms on the upper surface of the liquid. The scum remains on the glass. Both the scumming and the cloudy nature of the resulting formulation tends to put off some users.

However, the present inventors have found a unique stearate based lubricating composition which has been found to be extremely efficacious as a tableting excipient. More importantly, however, liquids formed by the use of liquid dissolvable effervescent tablets incorporating this lubricant do not exhibit the cloudiness or scumming otherwise associated with magnesium stearate based lubricants.

In general, the lubricant includes the mixture of a polyol which is generally low molecular weight polyalkylene glycol, a stearate and a small amount of a surface active agent. Polyethylene glycol or other generally low molecular weight polyalkylene glycols may be used as the polyol. The term lower molecular weight in accordance herewith generally means that the average molecular weight of the polyalkylene glycol used is below about 6000. Other compounds which may be useful include glycerine, glycerol, lower molecular weight alkylene glycols and the like may also be used. Any stearate may be administered as a part of this lubricant formulation. This includes stearates conventionally used for tableting aids such as magnesium stearate, calcium stearate, sodium stearate, potassium stearate, sucrose stearate and the like.

As a surface active agent, sodium lauryl sulfate may be used. Other surface active agents include edible surfactants and detergents such as docusate sodium. A preferred formulation which has been found useful includes polyethylene glycol 3350 in an amount of about 35 mg, magnesium stearate in an amount of 1.5 mg, and sodium lauryl sulfate in an amount of 0.15 mg, all used in a tablet having a final weight of 1,350 mg. Generally, however, the amount of surface active agent used will range from between about 0.1 and about 0.2 mg, the amount of stearates will range from between about 1 mg and about 2 mg and the polyalkylene glycol will be provided in an amount which will range from between about 20 mg and about 100 mg, per dose. Thus the ratio of the stearate to the surface active agent to the polyol ranges from between about 10:1:200 to about 20:2:1000. The amounts of these ingredients may vary widely, even outside of these ranges, particularly when different combinations of polyols, stearates and surface active agents are used. However, if too little stearate is used, there will not be sufficient lubrication. If too much is used, scumming and cloudiness may result. Similarly, if not enough surface active agent are used, a degree of film may be apparent. If too much surface active agent is used, then the resulting liquid may exhibit foaming. The upper limit of the polyol is not very important. However, if not enough polyol is used, then lubrication efficiency may be lost.

Because of the desirable properties of the present invention, and in particular, the compressibility of the particulate effervescent couple of the present invention, tablets can be manufactured by generally well-known tableting procedures. In common tableting processes, material which is to be tableted is deposited into a cavity, and one or more punch members are then advanced into the cavity and brought into intimate contact with the material to be pressed, whereupon compressive force is applied. The material is thus forced into conformity with the shape of the punches and the cavity. Hundreds, and even thousands, of tablets per minute can be produced in this fashion. Of course, by the practice of the present invention, it is possible to use lower quantities of binder and/or tableting pressure when compared to similar formulations. Various tableting methods, well known to those skilled in the art, are comprehensively discussed throughout the aforementioned Lieberman text.

In accordance with the present invention, however, effervescent tablets can be produced by mixing an amount of an active or pharmaceutical agent with a particulate effervescent couple produced in accordance with the present invention. The ratio of the base coated acid to the active agent has been previously described. Optionally, at least one binder and the magnesium stearate tableting lubricant described herein are also mixed with the active ingredient and effervescent couple. To the extent necessary or desirable, flavors and/or colorants can also be added at this point. Thereafter, portions of the mixture are then compressed in a tablet press under pressure of between about 0.2 and about 10.0 tons. The resulting effervescent tablet is relatively rapidly dissolvable in the mouth or in liquid. At the same time, the tablet is capable of withstanding conventional packaging, shipping and handling without cracking, chipping or disintegrating.

In general, tablets are compressed at a pressure of between about 0.1 and about 10.0 tons. More preferably, however, the amount of compressive force used to produce tablets in accordance with the present invention ranges from between about 0.4 to about 6 tons.

Materials to be incorporated in the tablets, other than the microparticles and the particulate effervescent couple, may be pretreated to form granules that readily lend themselves to tableting. This process is known as granulation. As commonly defined, "granulation" is any process of size enlargement whereby small particles are gathered together into larger, permanent aggregates to yield a free-flowing composition having a consistency suitable for tableting. Such granulated compositions may have consistency similar to that of dry sand. Granulation may be accomplished by agitation in mixing equipment or by compaction, extrusion or globulation.

In accordance with another aspect of the present invention, it is possible to include microparticles such as microcapsules or absorbates into these pharmaceutical dosage forms. Microparticles may be useful to provide an additional level of taste-masking for particularly objectionable medicaments, to further enhance the stability of, for example, an acid sensitive pharmaceutically active agent, to protect a material which would be sensitive to the base coating from reaction therewith, and the like. Microparticulate such as, for example, rupturable microcapsules and microparticles which are subject to rapid release, are disclosed in U.S. Pat. No. 5,178,878 as are procedures for manufacturing such microparticles. The text of U.S. Pat. No. 5,178,878 is hereby incorporated by reference. Absorbates can also be used.

The foregoing will be better understood with reference to the following examples. These examples are for the purposes of illustration. They are not to be considered limiting as to the scope and nature of the present invention.

Degradation of active ingredients is undesirable in any dosage form. Overall, it can be said that more than 5% product degradation is unacceptable, and for the most part more than 3% is undesirable. For $H_2$ antagonists, as well as other active compounds, testing at accelerated conditions gives an indication of the stability of the active ingredient. Accelerated conditions are generally defined as 40° C. and 75% relative humidity for 3 months. This equals 24 months of expiration dating for the product when stored at room temperature conditions. We have found that increased temperatures, particularly with the $H_2$ antagonists of 50° C. for as little as one month results in a good indication of stability. In general, degradation after 1 month at 50° C. should be no greater than 1% to assure that degradation after 3 months at 40° C. will not exceed 3%.

EXAMPLE 1

An environment of less than 25 grains of moisture per pound of air was utilized for the process.

A vacuum granulator of 50 liter capacity capable of tilting 180°, 90° on either side of vertical, comprising a thermostatable jacketed vessel connected to a vacuum pump and heating water source set at 80° C., an aperture for charging liquids in dispersed form, a variable speed mixing device assuring homogeneous mixing of the ingredients, a telescoping chopping device used to size the mixture of ingredients during granulation was used. In fact, a Zanchetta ROTO-50-P granulator was used. 11.4 kg of granular citric acid and 9.6 kg of powdered sodium bicarbonate were added to the granulator directly. The ingredients were mixed with the propeller on at 250 RPM and the chopper on for sizing for at least 2 minutes. 150 ml of de-ionized water was introduced by pressurizing a tank containing the water with air, and using the air pressure to force the water through a spray nozzle directly into the vessel while mixing. After 3 minutes, an additional 150 ml of de-ionized water was added to the vessel and the mixture was allowed to react for an additional 5 minutes. At the end of 5 minutes from the second water addition, the tilt was started for the vessel, the chopper was turned off, and the propeller was slowed to 20 RPM. When 11 minutes has elapsed from the time of second addition of water to the vessel, heat was applied to the jacket of the vessel, and the vacuum was turned on. When the temperature of the ingredients in the vessel reached 50° C., the tilting and the vacuum was turned off, and the chopper was turned on and the propeller speed was increased to 250 RPM for 5 minutes. At the end of 5 minutes, the chopper was turned off, the tilt was turned on, the vacuum was turned on, and the propeller was used 2 minutes, paused 6 minutes in sequence for the remainder of the process. When the product temperature reached 80° C., a sample was removed and if the moisture content of the granulation was less than 0.08%, cooling water was circulated through the vessel jacket until a temperature below 45° C. was reached.

The granulation was then discharged and stored in an environment of less than 25 grains of moisture per pound of air. An effervescent couple having a total yield of 75%–76% was resultant from the process

EXAMPLE 2

In an environment maintained at not more than 25 grains of moisture per pound of air, 120 grams of famotidine, 13,800 grams of the effervescent couple of Example 1, sodium lauryl sulfate 1.8 gm, polyethylene glycol 380 grams and magnesium stearate 18 grams, along with lemon flavor and sweetener were blended and compressed into tablets weighing 1,344 mg each containing famotidine. To determine the stability of the tablets, they were packaged into pouches having the following structure: 25 lb. pouch paper (outermost layer), 15 lb. polyethylene, 0.001" foil (moisture barrier), 12 lb. Surlyn (innermost heat seal layer). These were then sealed and placed at 50° C. and tested after one month of storage. The amount of degradation assayed was reported at 0.382% of the total 10 mg of active ingredient added.

EXAMPLE 3

An effervescent granulation process was carried out as in Example 1 except the amount of time between the second addition of water and the time at which vacuum was applied to the mixture was 8 minutes. The remainder of the process was followed as in Example 1.

A total yield of between 79% and 81% resulted.

EXAMPLE 4

120 grams of famotidine, 13,800 grams of the effervescent couple of Example 3, sodium lauryl sulfate 1.8 gm, polyethylene glycol 380 grams and magnesium stearate 18 grams, along with lemon flavor and sweetener were blended and compressed into tablets weighing 1,344 mg each containing 10 mg of famotidine. To determine the stability of the tablets, they were packaged into pouches which constructed as follows from top to bottom: 25# pouch paper, 15# polyethylene, 0.001" foil, 12# Surlyn. These were then sealed and placed at 50° C. and tested after one month of storage. The amount of degradation assayed ranged from 2.2% to 4.1% of the 10 mg of the total active added.

EXAMPLE 5

An effervescent granulation process was carried out as in Example 1 except the amount of time between the second addition of water and the time at which vacuum was applied to the mixture was 5 minutes. The remainder of the process was followed as in Example 1.

A total yield of between 82% and 87% resulted.

EXAMPLE 6

120 grams of famotidine, 13,800 grams of the effervescent couple of Example 5, sodium lauryl sulfate 1.8 gm, polyethylene glycol 380 grams and magnesium stearate 18 grams, along with lemon flavor and sweetener were blended and compressed into tablets weighing 1,344 mg each containing 10 mg of famotidine. To determine the stability of the tablets, they were packaged into pouches which constructed as follows from top to bottom: 25# pouch paper, 15# polyethylene, 0.001" foil, 12# Surlyn. These were then sealed and placed at 50° C. and tested after one month of storage. The amount of degradation assayed was in excess of 25% of the 10 mg of the total active added.

EXAMPLE 7

An effervescent granulation process was carried out as in Example 1 except the amount of time between the second addition of water and the time at which vacuum was applied to the mixture was 9 minutes, and the second addition of water was 125 ml. The remainder of the process was followed as in Example 1.

A total yield of between 78% and 80% resulted.

EXAMPLE 8

120 grams of famotidine, 13,800 grams of the effervescent couple of Example 7, sodium lauryl sulfate 1.8 gm, polyethylene glycol 380 grams and magnesium stearate 18 grams, along with lemon flavor and sweetener were blended and compressed into tablets weighing 1,344 mg each. To determine the stability of the tablets, they were packaged into pouches which constructed as follows from top to bottom: 25# pouch paper, 15# polyethylene, 0.001" foil, 12# Surlyn. These were then sealed and placed at 50° C. and tested after one month of storage. The amount of degradation assayed was 1.6% of the 10 mg of the total active added.

EXAMPLE 9

240 grams of famotidine, 13,800 grams of the effervescent couple of Example 1, sodium lauryl sulfate 1.8 gm, polyethylene glycol 380 grams and magnesium stearate 18 grams, along with lemon flavor and sweetener were blended and compressed into tablets weighing 1,354 mg each containing 20 mg of famotidine. To determine the stability of the tablets, they were packaged into pouches which constructed as follows from top to bottom: 25# pouch paper, 15# polyethylene, 0.001" foil, 12# Surlyn. These were then sealed and placed at 50° C. and tested after one month of storage. The amount of degradation assayed was 0.7% of the 20 mg of the total active added.

EXAMPLE 10

480 grams of famotidine, 13,800 grams of the effervescent couple of Example 1, sodium lauryl sulfate 1.8 gm, polyethylene glycol 380 grams and magnesium stearate 18 grams, along with lemon flavor and sweetener were blended and compressed into tablets weighing 1,364 mg each containing 40 mg of famotidine. To determine the stability of the tablets, they were packaged into pouches which constructed as follows from top to bottom: 25# pouch paper, 15# polyethylene, 0.001" foil, 12# Surlyn. These were then sealed and placed at 50° C. and tested after one month of storage. The amount of degradation assayed was 0.64% of the 40 mg of the total active added.

EXAMPLE 11

210 grams of ranitidine hydrochloride, 1,437.5 grams of the effervescent couple of Example 1, sodium lauryl sulfate 0.19 gm, polyethylene glycol 43.8 grams and magnesium stearate 1.9 grams, along with lemon flavor and sweetener were blended and compressed into tablets weighing 1,624 mg each and containing 150 mg of ranitidine base. To determine the stability of the tablets, they were packaged into pouches which constructed as follows from top to bottom: 25# pouch paper, 15# polyethylene, 0.001" foil, 12# Surlyn. These were then sealed and placed at 50° C. and tested after two weeks of storage. There was no detectable degradation of the active component in this formulation.

EXAMPLE 12

In a vacuum granulator of 600 liter capacity capable of tilting 180° to the vertical, comprising a thermostatable jacketed vessel connected to a vacuum pump and heating water source set at 80° C. an aperture for charging liquids in dispersed form, a variable speed mixing device assuring homogeneous mixing of the ingredients, a telescoping chopping device used to size the mixture of ingredients during granulation, 136.8 kg of granular citric acid and 115.2 kg of powdered sodium bicarbonate are added directly. The ingredients were mixed with the propeller on at 80 RPM and the chopper on for sizing for at least 2 minutes. 1275 ml of de-ionized water was introduced by pressurizing a tank containing the water with air, and using the air pressure to force the water through a spray nozzle directly into the vessel while mixing. After 3 minutes, an additional 1275 ml of de-ionized water was added to the vessel and the mixture was allowed to react for an additional 5 minutes. At the end of 5 minutes from the second water addition, the tilt was started for the vessel, the chopper was turned off, and the propeller was slowed to 20 RPM.

When 11 minutes had elapsed from the time of second addition of water to the vessel, heat was applied to the jacket of the vessel, and the vacuum was turned on. When the temperature of the ingredients in the vessel reached 50° C., the tilting and the vacuum were turned off, and the chopper was turned on and the propeller speed was increased to 250 RPM for 5 minutes. At the end of 5 minutes, the chopper was turned off, the tilt was turned on, the vacuum was turned on, and the propeller was used 2 minutes, paused 6 minutes in sequence for the remainder of the process. When the product temperature reached 80° C., a sample was removed and if the moisture content of the granulation was less than 0.08%, cooling water was circulated through the vessel jacket until a temperature below 45° C. was reached.

The granulation was then discharged and stored in an environment of less than 25 grains of moisture per pound of air. An effervescent couple having a total yield of 75%–76% was resultant from the process.

EXAMPLE 13

120 grams of famotidine, 13,800 grams of the effervescent couple of Example 12, sodium lauryl sulfate 1.8 gm, polyethylene glycol 380 grams and magnesium stearate 18 grams, along with lemon flavor and sweetener were blended and compressed into tablets weighing 1,344 mg each containing 10 mg of famotidine. To determine the stability of the tablets, they were packaged into pouches which constructed as follows from top to bottom: 25# pouch paper, 15# polyethylene, 0.001" foil, 12# Surlyn. These were then sealed and placed at 50° C. and tested after one month of storage. The amount of degradation assayed was 0.5% of the 10 mg of the total active added. After 6 months of storage at 40° C., the amount of degradation was measured at 0.3% of the total amount of active added.

The principles, preferred embodiments, and modes of operation of the present invention have been described in the foregoing specification. The invention which is intended to be protected herein, however, is not to be construed as limited to the particular embodiments disclosed, since these are to be regarded illustrative rather than restrictive. Variations and changes may be made by others without departing from the spirit and scope of the invention.

What is claimed is:

1. A stabilized effervescent dosage form comprising:

an acid sensitive pharmaceutically active agent; and intimately mixed therewith, a particulate effervescent couple, said effervescent couple consisting essentially of a solid core of an edible acid and a coating of an edible base, the amount of said base used in forming said coating being less than a stoicheometric amount relative to said edible acid, said edible acid core and said edible base coating being reacted such that at least some free unreacted edible acid remains, wherein said coating of said base retards reaction between said edible acid and said acid sensitive pharmaceutically active agent which would lessen the activity of said dosage form;

said dosage form having an acid neutralization capacity of less than about 5.0.

2. The stabilized effervescent dosage form of claim 1, wherein said acid sensitive pharmaceutically active agent is an acid sensitive gastrointestinally active agent.

3. The stabilized effervescent dosage form of claim 2, wherein said acid sensitive gastrointestinally active agent is an antiulcerative agent.

4. The stabilized effervescent dosage form of claim 3, wherein said antiulcerative agent is selected from the group consisting of ranitidine, cimetidine, famotidine, nizatidine, etintidine, lupitidine, mifentidine, niperotidine, roxatidine, sufotidine, tuvatidine, zaltidine, pharmaceutical salts thereof, and mixtures thereof.

5. The stabilized effervescent dosage form of claim 1, wherein said edible acid is citric acid.

6. The stabilized effervescent dosage form of claim 1, wherein said citric acid used to produce said particulate effervescent couple is a particulate of size such that 100% will be retained on a 60 mesh screen.

7. The stabilized effervescent dosage form of claim 1, wherein said edible base is a carbonate or bicarbonate.

8. The stabilized effervescent dosage form of claim 7, wherein said edible base is selected from the group consisting of sodium bicarbonate and potassium bicarbonate.

9. The stabilized effervescent dosage form of claim 1, wherein said edible base used to coat said core of edible acid has a particle size such that 99% is passed through a 100 mesh screen.

10. The stabilized effervescent dosage form of claim 1, wherein said particulate effervescent couple is produced from a mixture of between about 49% and about 60% of said edible acid and between about 51% and about 40% of said edible base based on the weight of citric acid and bicarbonate.

11. The stabilized effervescent dosage form of claim 10, wherein said particulate effervescent couple is produced from a mixture of between about 52% and about 56% by weight of said edible acid and between about 48% and about 44% by weight of said edible base.

12. The stabilized effervescent dosage form of claim 2, wherein said ratio of said acid sensitive gastrointestinally active agent to said effervescent couple is from between about 1:300 to about 1.0:0.25.

13. The stabilized effervescent dosage form of claim 12, wherein said ratio of said acid sensitive gastrointestinally active agent to said effervescent couple is from between about 1:230 to about 1:1.

14. The stabilized effervescent dosage form of claim 13, wherein said ratio of said acid sensitive gastrointestinally active agent to said effervescent couple is from between about 1:125 to about 1:10.

15. The stabilized effervescent dosage form of claim 1, wherein said acid neutralization capacity ranges from between about 0.2 to less than about 5.

16. The stabilized effervescent dosage form of claim 15, wherein said acid neutralization capacity ranges from between about 2.5 to about 4.5.

17. A process of producing a particulate effervescent couple having an acid neutralization capacity of less than about 5.0, comprising the steps of:

charging at least one particulate edible acid and at least one particulate edible base selected from the group consisting of sodium bicarbonate and potassium bicarbonate into a reactor, said edible base having a particle size which is less than the particle size of said particulate edible acid;

mixing said particulate;

adding liquid to said particulate in said reactor while said mixing continues;

allowing said particulate to react in the presence of said liquid for a period of time so as to form a coating of said edible base around the particulate edible acid;

terminating said reaction by applying vacuum and heat to said reactor while physically tilting said reactor so as to provide for rapid and even liquid removal from said particulate and so as to prevent a coating of said edible base from being abraded from said particulate edible acid; and discharging said particulate, whereby said particulate edible acid is coated with said edible base and has an acid neutralization capacity of less than about 5.0.

18. The process of claim 17, wherein said edible acid originally has a particle size such that 100% thereof will be retained upon a 60 mesh screen.

19. The process of claim 18, wherein said edible base initially has a size such that 99% of particulate thereof will pass through a 100 mesh screen.

20. The process of claim 17, wherein 44% to about 60% of the particulate charged to the reactor is an edible acid and 56% to about 40% by weight of the particulate by weight is said edible base.

21. The process of claim 20, wherein between about 49% and about 60% of said particulate charged to said reactor is edible acid and between about 51% and about 40% of said particulate charged to said reactor is said edible base.

22. The process of claim 21, wherein between about 52% and about 56% of said particulate charged to said reactor is edible acid and between about 44% and about 48% of said particulate charged to said reactor is said edible base.

23. The process of claim 17, wherein at least about 31% of said acid groups charged to said reactor will remain unreacted by the quantity of base charged thereto.

24. The process of claim 17, wherein said liquid is added in a plurality of discrete intervals prior to said step of applying vacuum and heat.

25. The process of claim 24, wherein between about 1 to about 20 ml of liquid is added to said reactor per every kg of particulate.

26. The process of claim 25, wherein between about 8 to about 12 ml of liquid is added to said reactor per every kg of particulate.

27. The process of claim 17, wherein said liquid is water.

28. The process of claim 17, wherein sufficient vacuum is applied such that the pressure within the reactor is less than atmospheric pressure.

29. The process of claim 28, wherein sufficient vacuum is applied such that the pressure within the reactor is less than about 20 inches of mercury.

30. The process of claim 17, wherein said reactor is heated to between about 60° C. and about 100° C.

31. The process of claim 30, wherein said reactor is heated to between about 80° and about 95° C.

32. The process of claim 17, wherein said reactor is tilted to an angle of greater than between about 75° from vertical.

33. The process of claim 32, wherein said interval is at least about once per 5 min.

34. The process of claim 33, wherein said interval is at least about once per minute.

35. A product resulting from the process of claim 17.

36. A product resulting from the process of claim 22.

37. A process of making an effervescent tablet comprising the steps of:

mixing an active agent with a particulate effervescent couple produced in accordance with the process of claim 20, wherein said ratio of said active agent to said effervescent couple is from between about 1:300 to about 1:0.25;

optionally adding at least one lubricant in an amount of between about 0.1 and about 1.5 weight percent of said tablet;

optionally adding at least one binder in an amount of between about 2 and about 15 percent by weight of said tablet; and compressing said mixture in a tablet press under a pressure of between about 0.2 to about 10.0 tons, wherein the resulting effervescent tablet being relatively rapidly dissolvable in the mouth or in liquid while at the same time being capable of withstanding conventional packaging, shipping, and handling without cracking, end capping, or disintegrating.

* * * * *